United States Patent [19]

Jang

[11] Patent Number: 4,959,053

[45] Date of Patent: Sep. 25, 1990

[54] AUTOMATIC STOPPING DEVICE FOR THE INTRAVENOUS DRIP

[76] Inventor: Cheng-Houng Jang, 5 Alley 39, Lane 81, Leou Chyau West Rd., Gang-Shan Jen, Kaohsiung Hsien, Taiwan

[21] Appl. No.: 134,064

[22] Filed: Dec. 17, 1987

[51] Int. Cl.5 ............................................. A61M 1/00
[52] U.S. Cl. .................................... 604/127; 604/411; 604/254
[58] Field of Search ............... 604/127, 403, 405, 411, 604/414, 251, 254, 256; 137/399

[56] References Cited

U.S. PATENT DOCUMENTS

| | | | |
|---|---|---|---|
| 3,227,173 | 1/1966 | Bernstein | 604/127 |
| 3,465,784 | 9/1969 | Cofoid | 604/127 |
| 3,822,700 | 7/1974 | Pennington | 604/414 |
| 3,982,534 | 9/1976 | Buckman | 604/127 |
| 4,055,176 | 10/1977 | Lundquist | 604/254 |
| 4,203,463 | 5/1980 | Ponlot et al. | 604/127 |
| 4,449,976 | 5/1984 | Kamen | 604/127 |
| 4,475,914 | 10/1984 | Portnoff | 604/414 |
| 4,640,306 | 2/1987 | Fan | 604/254 |

Primary Examiner—C. Fred Rosenbaum
Assistant Examiner—Kathleen A. Dailey
Attorney, Agent, or Firm—Larson and Taylor

[57] ABSTRACT

This invention relates to an intravenous drip, which has a dripping vessel, a cap, a valve, a connecting tube and a pointed bar been inserted in the solution bottle letting the solution in said bottle to flow down through a solution passage of said bar into said dripping vessel, and said valve with a hollow cone to float on the solution level in said dripping vessel and to blow the flow of the solution by means of the circumferential surface of said hollow cone able to touch the upper inside rim of the connecting tube inserted in the said linking tube of the dripping vessel as the solution level therein gradually goes down.

5 Claims, 3 Drawing Sheets

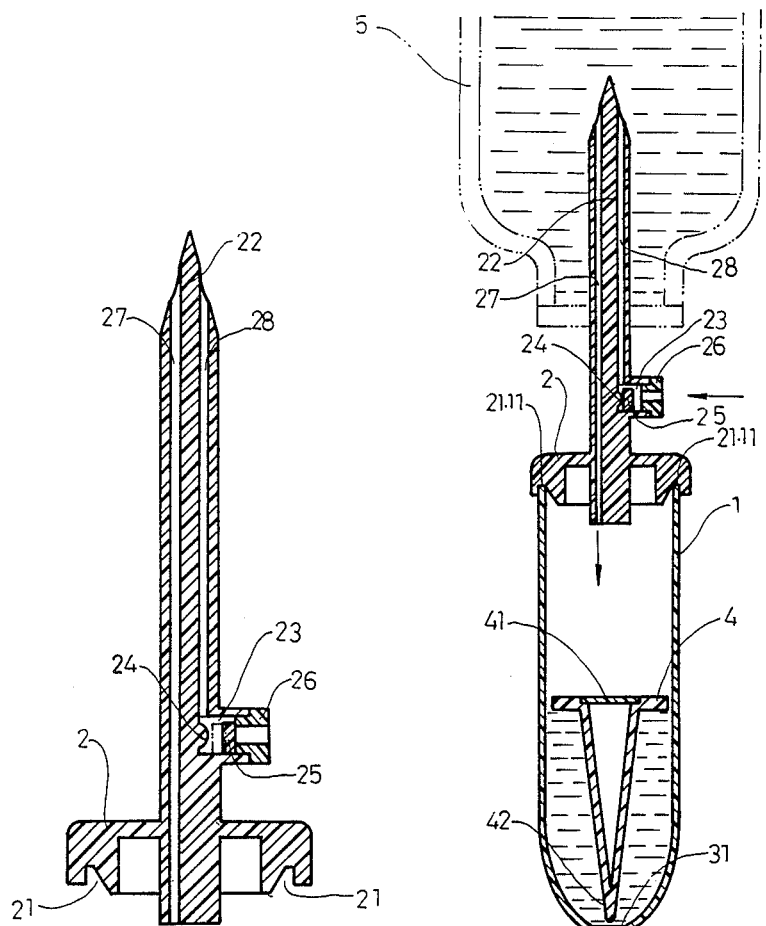

AUTOMATIC STOPPING DEVICE FOR THE INTRAVENOUS DRIP

BACKGROUND OF THE INVENTION

Conventional devices for the intravenous drip are generally not provided with automatic stopping devices, one must take care whether the medical solution is going to run out or not to stop dripping lest air should flow into the patient's vein.

An automatic stopping device is known provided in the dripping vessel, which can float on the solution level and fall down with it when the solution is going to run out. But the float is round and rather hard to make. Especially its material should have a proper weight and a buoyancy such as plastics. This known float is assembled with two half balls with a circumferential connecting line so the function of stopping solution cannot be completely accomplished. This product, therefore, could hardly be commercially successful.

Besides, all the known solution bottles contain an air tube which is to be pricked through by a needle in order to let the solution drip down into the dripping vessel. This air tube should be made to have its top end to protrude above solution level after said bottle is hung upside down, as otherwise the solution can never drip down smoothly. Consequently it is rather a complicated job to provide the solution bottle with said air tube.

SUMMARY OF THE INVENTION

In order to solve the problems in the prior art mentioned above, the present invention provides an automatic stopping device for the intravenous drip which can be used without the air tube in the solution bottle, in order to improve the shortcoming above-mentioned, to simplify the work of stopping or resuming the dripping of the solution and to lessen the cost of manufacturing it.

This automatic stopping device for the intravenous drip includes a soft transparent dripping vessel made of plastic or rubber, a cap covering the upside opening of said dripping vessel and provided with a pointed bar with a pointed end to insert in the solution bottle. An air passage and a solution passage are provided lengthwise in said bar, said air passage being used for air to pass in the solution bottle, said solution passage being used for the solution to flow down into the dripping vessel. A valve provided with a long hollow cone extending downward is contained in the dripping vessel; the valve can float with its flat part on the solution level and the circumferential surface of said cone can insert in the outlet stopping the solution from flowing down when the solution level goes down to a certain point.

BRIEF DESCRIPTION OF THE DRAWINGS

FIG. 2 is a cross-sectional view of the cap with the pointed bar in this invention.

FIG. 3 is a functional view of the device in this invention.

DETAILED DESCRIPTION OF THE INVENTION

Figure 1:
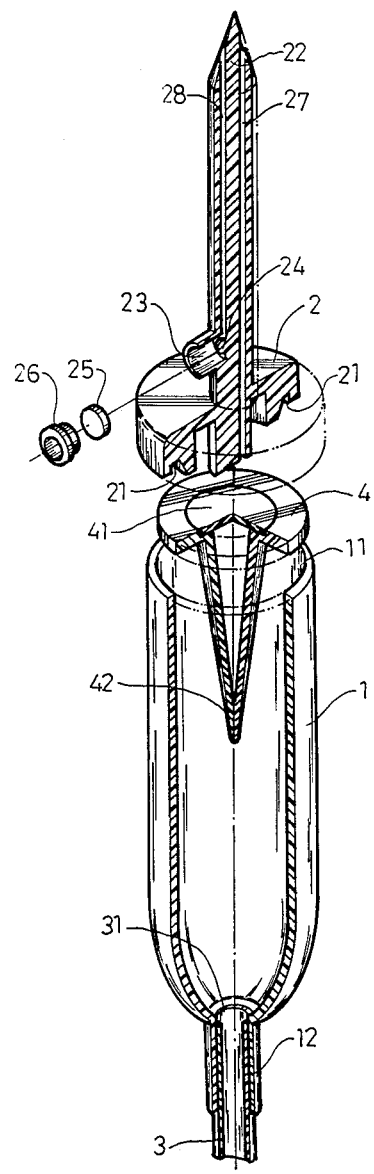
FIG. 1 is a dismantled view of the automatic stopping device for the intravenous drip in this invention.

This automatic stopping device for the intravenous drip comprises dripping vessel 1, cap 2, connecting tube 3 and valve 4 as shown in FIG. 1.

Dripping vessel 1 made of soft and transparent plastics or rubber is shaped as a cylinder provided with opening 11 at the upper end for cap 2 to glue together, and short linking tube 12 at the lower end extending downward for connecting tube 3 to combine with. Connecting tube 3 has a flat top end just corresponding to the outlet at the curved bottom of dripping vessel 1 for combining with linking tube 3.

Valve 4 provided with disc 41 and a long hollow cone 42 extending down from disc 41 is contained in dripping vessel 1 for floating with disc 41 on the solution level and blocking said outlet of dripping vessel 1 with the circumferential surface of the cone 42 properly touching the inside rim 31 of the top end of connecting tube 3 when valve 4 goes down along with the solution level to a certain point. And the circumferential surface of the cone 42 is extremely soft and smooth. Cap 2 shown in FIGS. 1 and 2 is provided with circumferential groove 21 at the lower end fitting and being adhered with the rim of opening 11 of dripping vessel 1, and pointed bar 22 extending up from its center which is provided with crosswise round tube hole 23 near the body of cap 2 and with semi-circular protrusion 24 at the bottom of round tube hole 23. Inside round tube hole 23 is set ring 25 which can move rightward and leftward therein (as viewed in FIGS. 2-5) and in round tube hole 23 is fixed hollow stopper 26.

Pointed bar 22 is also provided with lengthwise solution passage 27 from the upper end to the lower end for the solution in the solution bottle to flow down in dripping vessel 1 and with air passage 28 from the upper end to round tube hole 23 for the atmospheric air to flow into the solution bottle.

The purpose of setting ring 25 inside round tube hole 23 is to prevent the solution from escaping therefrom. Dripping vessel 1 has at first to be pressed with fingers forcing the air inside vessel 1 to flow through solution passage 27 into the solution bottle and through connecting tube 3 when this device is inserted in the solution bottle for applying intravenous drip. As the air has entered the solution bottle, ring 25 is forced to move rightward to block the hole of hollow stopper 26 so the solution could not flow out therefrom. When the pressure in dripping vessel 1 is removed, the solution gradually begins to flow down from the bottle into dripping vessel 1 and then ring 25 moves leftward and is stopped by protrusion 24 so as not to block air passage 28 letting the atmospheric air through hollow stopper 26 and air passage 28 into solution bottle.

Connecting tube 3 is a common soft plastic tube to connect with dripping vessel 1 at the upper end and an injection needle at the lower end and its outside diameter just conforms the inside diameter of linking tube 12 of dripping vessel 1, both of them being adhered together. Besides, top rim 31 of said tube 3 has a smooth flat surface for the circumferential surface of cone 42 of valve 4 to touch so that the passage of the solution can be blocked.

Next, valve 4 made of plastics is provided with a round flat body, hollow cone 42 extending downward from the body and flat disc 41 glued on the body making up a hollow space inside cone 42 so as to float in the solution.

FIG. 3 shows this device in practical use; pointed bar 22 is inserted in the solution bottle 5 put upside down and the solution drips down slowly through solution passage 27 into dripping vessel 1. The solution continues to drip down into dripping vessel causing valve 4 to float and rise up along with the solution level until the solution level reaches to such a height that the solution can be let out of connecting tube 3.

Figure 4:
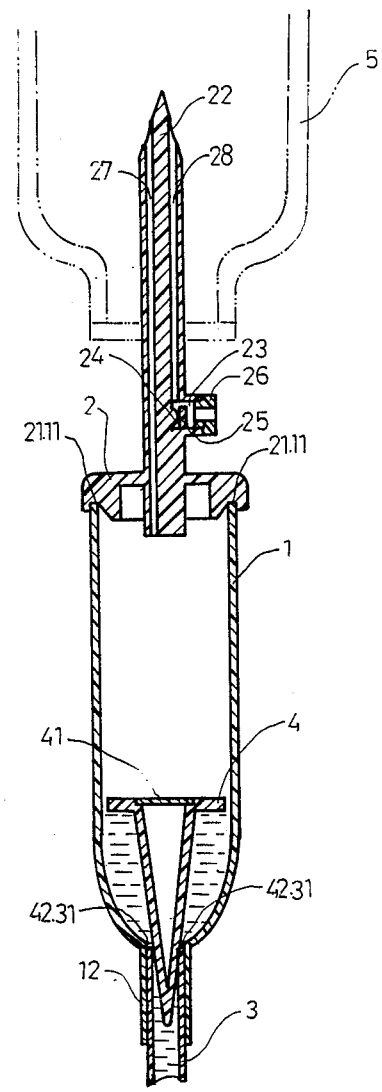
FIG. 4 is another functional view of the device in this invention.
Figure 5:
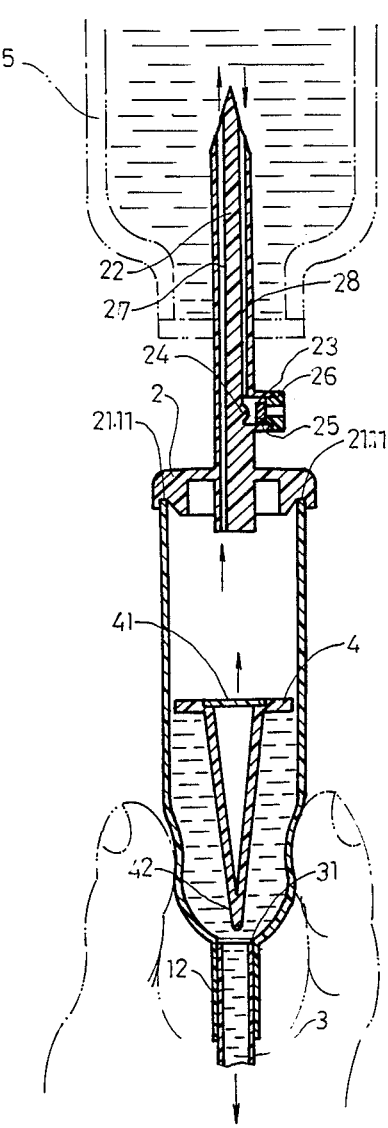
FIG. 5 is another functional view of the device in this invention.

When all the solution in the solution bottle 5 has flowed out and the solution level in dripping vessel 1 is gradually going down as shown in FIG. 4, valve 4 is also falling down to make the circumferential surface of cone 42 finally touch around the top rim 31 of connecting tube 3 to block the passage of the solution so that air can never be injected into a human body.

In case the intravenous drip still has to continued after one bottle has been used up, then dripping vessel 1 should be pinched with the fingers at the place below valve 4 making the solution level and valve 4 rise up lest cone 42 of valve 4 should block connecting tube 3. Therefore, the solution can continuously be injected in the human body and a new solution bottle can be fixed to take the place of an old bottle.

In short, this device has a simple structure and a cheaper cost than the conventional one. Its function in hampering the solution is quite accurate, and above all, resumption of injection is so simple as to be accomplished by pinching the dripping vessel with the thumb and the index finger. This device is more simple to operate than the conventional device provided with an air tube in the solution bottle, which air tube is not needed in this device.

What is claimed is:

1. A flow control device for an intravenous drip system, comprising:
    a dripping vessel of elongated generally cylindrical shape, the vessel being of a soft easily squeezable material, the said vessel having an upper opening adapted to be connected to a cap and a lower opening adapted to be connected to a connecting tube which leads to a patient which is to receive the intravenous liquid,
    a cap of a material harder than the material of the dripping vessel, said cap adhered to said upper opening, the cap having a pointed bar projecting away from the dripping vessel and adapted to be inserted into a medicine bottle containing solution, said pointed bar having a solution passageway for the flow of liquid from the medicine bottle to the dripping vessel,
    a valve element contained within the dripping vessel, said valve element being an elongated downwardly pointed cone of a buoyancy such that it floats in the liquid, the diameter of the top of the cone being less than the inside diameter of the dripping vessel such that liquid can flow around the said top, the valve element being of such a length, and of such a converging diameter that after a liquid reaches a predetermined level in the dripping vessel, a portion of the cone blocks the said lower opening while the said top is sufficiently far above the blocked lower opening that there is room between said lower openings and said top for the vessel to be squeezed by the fingers of the operator to force the valve element upward, while some residual liquid is still contained within the lower portion of the dripping vessel, to concurrently (1) force air up through the cap into the bottle to enhance initiation of liquid flow from the bottle downwardly into the dripping vessel and (2) raise the valve element to open the lower opening to allow the residual liquid to immediately commence flowing down through the lower opening.

2. A flow control device according to claim 1, said valve element being a hollow body, the base of the cone being defined by a circular disc which forms the said top of the valve element.

3. A flow control device according to claim 1, including a connecting tube connected to the inside of said lower opening of the dripping vessel, said connecting tube having a flat top rim at its upper end which is positioned to be engaged by the cone of the valve element to close off the lower opening.

4. A flow control device according to claim 1, said pointed bar also having an air passageway for the flow of air from the outside of the device into the medicine bottle, a valve means in said air passageway, said valve means comprising a small opening from the outside of the device into the air passageway, a chamber in the air passageway just inside from the small opening, a protrusion on the end of the chamber opposite from the small opening, a movable element in the chamber movable to a first position against the small opening to close off the air passageway to prevent the flow of any liquid from the medicine bottle through the small opening and a second position wherein the movable element lies against the protrusion to permit air to flow from outside, through the small opening, the chamber and the air passageway and into the medicine bottle.

5. A flow control device according to claim 4, said protrusion being a rounded protrusion, and the movable element being a disc shaped element movable back and forth within said chamber between said first and second positions.

* * * * *